(12) United States Patent
Lam et al.

(10) Patent No.: US 9,869,586 B2
(45) Date of Patent: Jan. 16, 2018

(54) SAMPLING HEADS FOR HANDHELD RAMAN SPECTROSCOPY DEVICES

(71) Applicant: TSI, Incorporated, Shoreview, MN (US)

(72) Inventors: Tony Lam, Irvine, CA (US); Kevin Pan, Irvine, CA (US)

(73) Assignee: TSI Incorporated, St. Paul, MN (US)

( * ) Notice: Subject to any disclaimer, the term of this patent is extended or adjusted under 35 U.S.C. 154(b) by 0 days.

(21) Appl. No.: 15/154,224

(22) Filed: May 13, 2016

(65) Prior Publication Data
US 2016/0334277 A1    Nov. 17, 2016

Related U.S. Application Data

(60) Provisional application No. 62/161,977, filed on May 15, 2015.

(51) Int. Cl.
*G01J 3/44* (2006.01)
*G01J 3/02* (2006.01)
*G01N 1/00* (2006.01)
*G01N 21/65* (2006.01)

(52) U.S. Cl.
CPC ........... *G01J 3/0291* (2013.01); *G01J 3/0272* (2013.01); *G01J 3/44* (2013.01); *G01N 1/00* (2013.01); *G01N 21/65* (2013.01); *G01N 2201/0221* (2013.01)

(58) Field of Classification Search
CPC .... G01J 3/44; G01J 3/02; G01J 3/4412; G01J 3/0272; G01J 3/0291; G01N 1/00
See application file for complete search history.

(56) References Cited

U.S. PATENT DOCUMENTS

| | | |
|---|---|---|
| 4,775,054 A | 10/1988 | Dixon |
| 6,621,574 B1 * | 9/2003 | Forney ...................... G01J 3/02 250/252.1 |
| 7,403,281 B2 | 7/2008 | Carron et al. |
| 7,505,128 B2 | 3/2009 | Zribi et al. |
| 7,542,138 B2 | 6/2009 | Gardner, Jr. |
| 7,548,310 B2 | 6/2009 | Gardner, Jr. et al. |
| 7,796,243 B2 | 9/2010 | Choo-Smith et al. |
| 7,929,131 B2 | 4/2011 | Lam et al. |
| 8,345,226 B2 | 1/2013 | Zhang |
| 8,699,020 B1 | 4/2014 | Zhou et al. |

* cited by examiner

*Primary Examiner* — Abdullahi Nur
(74) *Attorney, Agent, or Firm* — Kagan Binder, PLLC

(57) ABSTRACT

Various novel sampling heads and interface fittings are disclosed herein adapted for use with handheld RAMAN or other material evaluating devices or analyzers using radiation or electromagnetic energy to identify sampled materials. In particular, the interface fittings or members facilitate measurement of irregularly shaped or very small materials to be sampled.

20 Claims, 12 Drawing Sheets

SAMPLING HEADS FOR HANDHELD RAMAN SPECTROSCOPY DEVICES

CLAIM OF PRIORITY

The present nonprovisional patent application claims the benefit of and priority to, under 35 USC § 119(e), U.S. Provisional Patent Application No. 62/161,977, filed May 15, 2015, entitled "SAMPLING HEADS FOR HANDHELD RAMAN SPECTROSCOPY DEVICES," the entirety of which is incorporated herein by reference.

FIELD AND BACKGROUND

The invention is generally in the field of Raman spectroscopy (RAMAN) and more particularly to a sampling head for an apparatus and system designed for Raman spectroscopy measurements.

For various applications, methods are needed for determining the material constitution of a sample. One of the known methods is Raman spectroscopy (RAMAN), which involves shining a monochromatic light source, such as a laser, on a sample material and detecting the resulting scattered light. Most of the scattered light is the same frequency as the source. However, a very small amount of the scattered light (ca. 10-5% of the incident light intensity) is shifted in energy from the laser frequency due to interactions between the incident electromagnetic waves and the vibrational energy levels of the molecules in the sample. Plotting the intensity of this "shifted" light versus frequency results in a Raman spectrum of the sample.

The sample may in principle be solid, liquid or gaseous. In the case of a solid sample, the sample material or particle may of an irregular shape and/or difficult to hold while trying to focus the laser beam onto the sample's surface with a handheld or portable device. Efforts have been made to reduce the form factor of RAMAN devices into handheld devices, as evidenced by U.S. Pat. No. 7,505,128 to Zribi et al., and U.S. Pat. No. 8,699,020 to Zhou et al., however these devices still have not solved the problem of accurately identifying or evaluating samples of differing shapes and sizes. Therefore, there still exists a need for a handheld RAMAN device that addresses the aforementioned challenges.

SUMMARY

Various example embodiments described herein provide sampling heads and interface fittings adapted for use with handheld RAMAN or other material evaluating devices or analyzers using radiation or electromagnetic energy to identify sampled materials. In particular, the interface fittings or members facilitate measurement of irregularly shaped or very small materials to be sampled. One of the purposes of the embodiments of the invention is to provide steady and convenient approaches to handle, hold and clamp different, small and odd or irregularly shaped samples for RAMAN and Raman spectroscopy measurements and applications. Further, the embodiments provide a manner of sealing the measurements from environmental light interference and to optimize the laser energy at the sample collection areas. Furthermore, the devices and teachings herein provide a quick way to calibrate Raman spectroscopy systems.

The various embodiments described herein provide advantages to the user in: 1) the calibration standard provides a strong and broad spectrum signal at the low intensity collimated laser beam; 2) provide a permanent convenient manner to quickly obtain the system calibration; 3) the sampling members can hold a variety of different and irregularly shaped samples and seal the samples from environmental light; and 4) the sampling members provide a way to clean the lens tube without losing the pre-alignment. In short, the novel interface members provide the user with a steady and convenient way to hold samples, prevent light interference, a quick way to obtain system calibration and a convenient way to clean the lens tube that is not provided by prior art devices.

In one example embodiment, there is provided a sampling head assembly for use on a handheld spectroscopy device that includes an electromagnetic radiation source, an electromagnetic radiation detection and a processing module located within a housing having a housing exit for electromagnetic radiation and for capture of an emitted electromagnetic radiation from a sample material. The sampling head assembly of the spectroscopy device includes a collection interface member having a central aperture for placement over the housing exit and a calibration clamp member disposed adjacent to the collection interface member, the clamp member with an aperture disposed collinear with the central aperture of the collection interface member. The sampling head assembly further includes a sampling tube member disposed through and collinear with the calibration clamp member with a proximal end of the tube member disposed over the central aperture of the collection interface member and a sampling tube cover member disposed over a distal end of a sampling tube member, thereby forming the sampling head assembly. In a related embodiment, the sampling head assembly further includes a calibration clamp holder for holding and axially moving the calibration clamp member and a cover stopper member interposed between the sampling tube and the sampling tube cover member. The sampling head assemblies described herein operate with a spectrographic measurement device selected from the group consisting of Raman, LIBS, fluorescence and x-ray radiation.

In a related embodiment, the sampling head assembly further includes a concave member having an open end and an aperture opposite the open end, the concave member disposed adjacent to the sampling tube cover member with a portion of the sampling tube cover member protruding through the concave member aperture, wherein the concave member is adapted to reduce light interference during a spectrographic measurement. In various embodiments, the concave member has a concave structure with a shape selected from the group consisting of a concave plunger or bowl, a square box, a rectangular box and an elliptical bowl In this example embodiment, the sampling head assembly further includes a pellet holder assembly disposed over the sampling tube cover member, the pellet holder assembly including a pellet holder with a proximal end disposed on the tube cover member and a pellet holder cover disposed on a distal end of the pellet holder, wherein the pellet holder assembly reduces ambient light interference during a spectrographic measurement.

In yet another embodiment, the sampling head assembly further includes a clamping-type interface assembly disposed in contact with a distal end of the sampling tube cover member, the clamping-type interface assembly including an interface plug portion coupled to a first end of an elongate interposing member, the elongate interposing member coupled at a second end to a thumbscrew pad assembly, wherein the clamping-type interface assembly is adapted to clamp or grasp an irregularly shaped sampled material against the housing exit, thereby reducing light interference during a spectrographic measurement. In yet another example embodiment, there is provided a handheld Raman spectroscopy apparatus for performing spectrographic measurements on a sample material, the Raman handheld spectroscopy apparatus having a housing that includes an exit for electromagnetic radiation and for capture of an emitted electromagnetic radiation from the sample material. The Raman handheld apparatus includes a laser module for emitting electromagnetic radiation on the sample material, a spectrometer module for receiving and detecting electromagnetic radiation received from the sample material, and a processing module communicatively coupled to the laser module and the spectrometer module disposed within the housing, the processing module configured to control the energization of the laser module and processing of spectrographic measurements received from the spectrometer module. The handheld device further includes a housing-to-sample material interaction assembly disposed about the housing exit wherein a distal end of the interaction assembly is configured to receive interchangeable sampling heads that reduce light interference during a Raman measurement of sampled materials having different shapes and sizes. The interaction or sampling head assembly including a collection interface member having a central aperture for placement over the housing exit, a calibration clamp member disposed adjacent to the collection interface member with the clamp member having an aperture disposed therein that is collinear with the central aperture of the collection interface member. The head assembly further including a sampling tube member disposed through and collinear with the calibration clamp member with a proximal distal end of the tube member disposed over the central aperture of the collection interface member and a sampling tube cover member disposed over a distal end of a sampling tube member, a distal end of the tube cover member configured to receive the interchangeable sampling heads.

The novel features of the various embodiments the invention itself, both as to its construction and its method of operation, together with additional advantages thereof, will be best understood from the following description of specific embodiments when read in connection with the accompanying drawings.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1C:
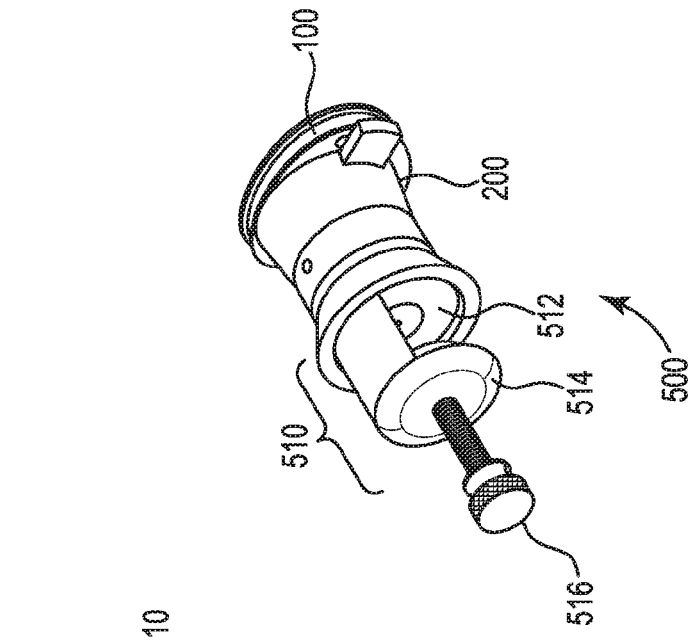
FIGS. 1A-1C illustrate perspective views of three (3) embodiments of sampling interface members or heads with a mounting sleeve configured for use in connection with a handheld RAMAN device according to an embodiment of the invention.
Figure 1B:
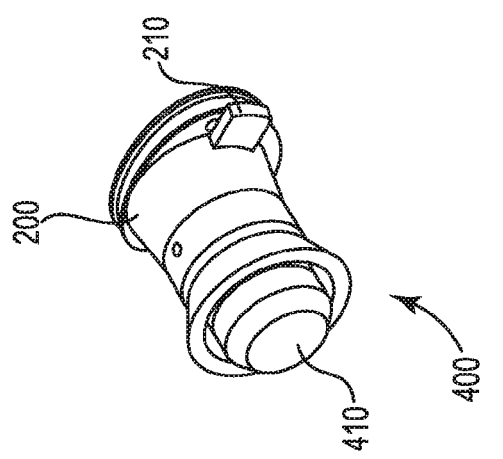
Figure 1A:
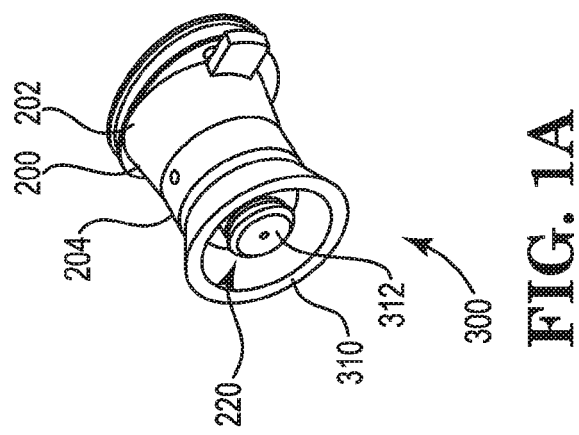
Figure 2A:
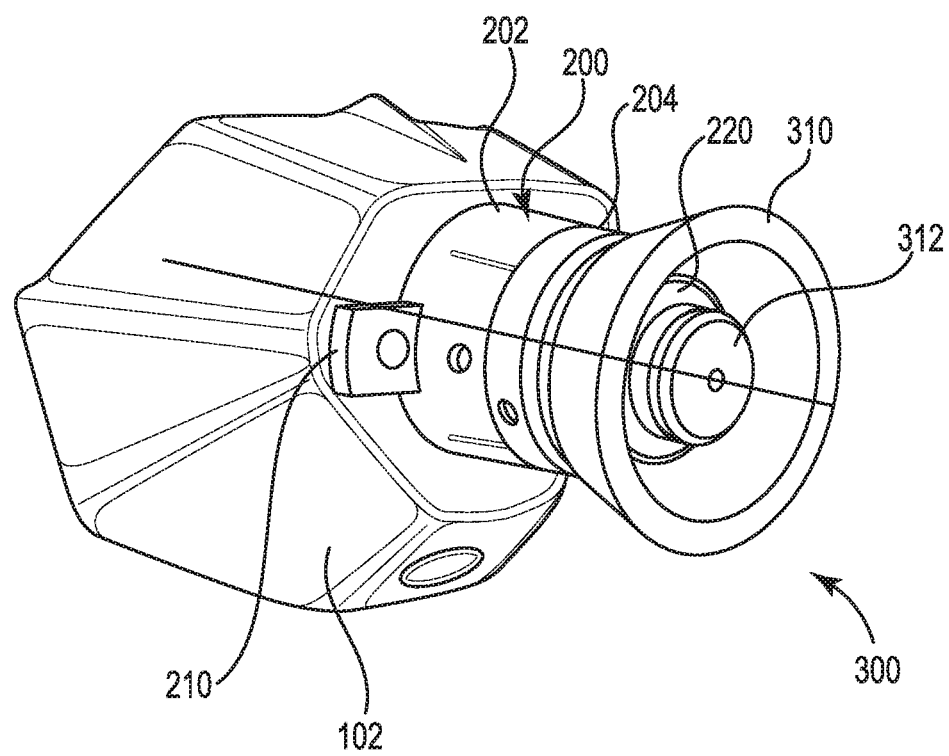
FIGS. 2A-2B illustrate perspective views of a first sampling interface member on a handheld device housing and a view of a portion of the first sampling member without the mounting sleeve according to an example embodiment of the invention.
Figure 2B:
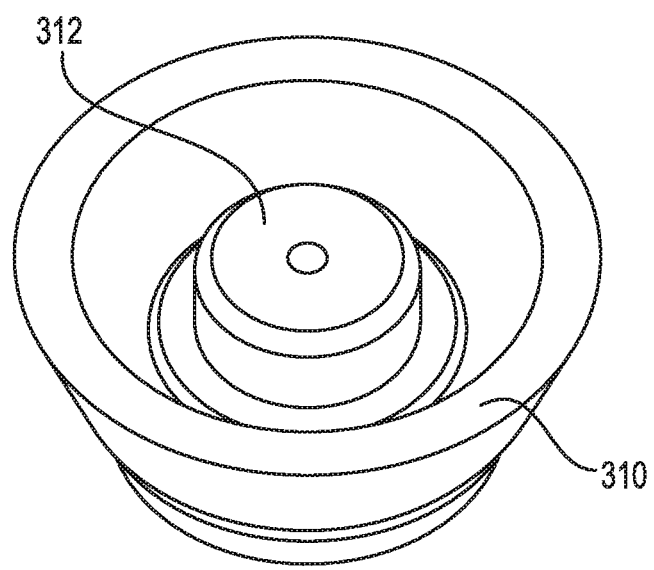

Referring now to FIGS. 1A-1C and FIG. 2A, there is illustrated views of three (3) example embodiments of sampling interface members (or collection interface members) 300, 400 and 500 with a mounting sleeve 200 configured for use in connection with a handheld RAMAN device according to an embodiment of the invention. In this example embodiment, mounting sleeve 200 is adapted to be secured at a proximal end 202 to an exit of a collection interface member 100 of a handheld RAMAN device 102 (partially shown in FIG. 2A) along with a calibration standard tab 210. At a distal end 204 of sleeve 200 is located a tube cover 220 adapted to hold one of the sampling interface member components described herein. In FIGS. 2A-2B there are illustrated perspective views of first sampling interface member 300 on handheld RAMAN device 102 and a concave portion or a concave plunger member (or tube cover) 310 and a tube cover or stopper 312 of the first sampling member, without the mounting sleeve, respectively, according to an example embodiment of the invention. In this example embodiment, the concave plunger member 310 helps to prevent ambient light interference by enveloping the sample material or at least the location on the sampled material surface that is being tested.

Figure 3A:
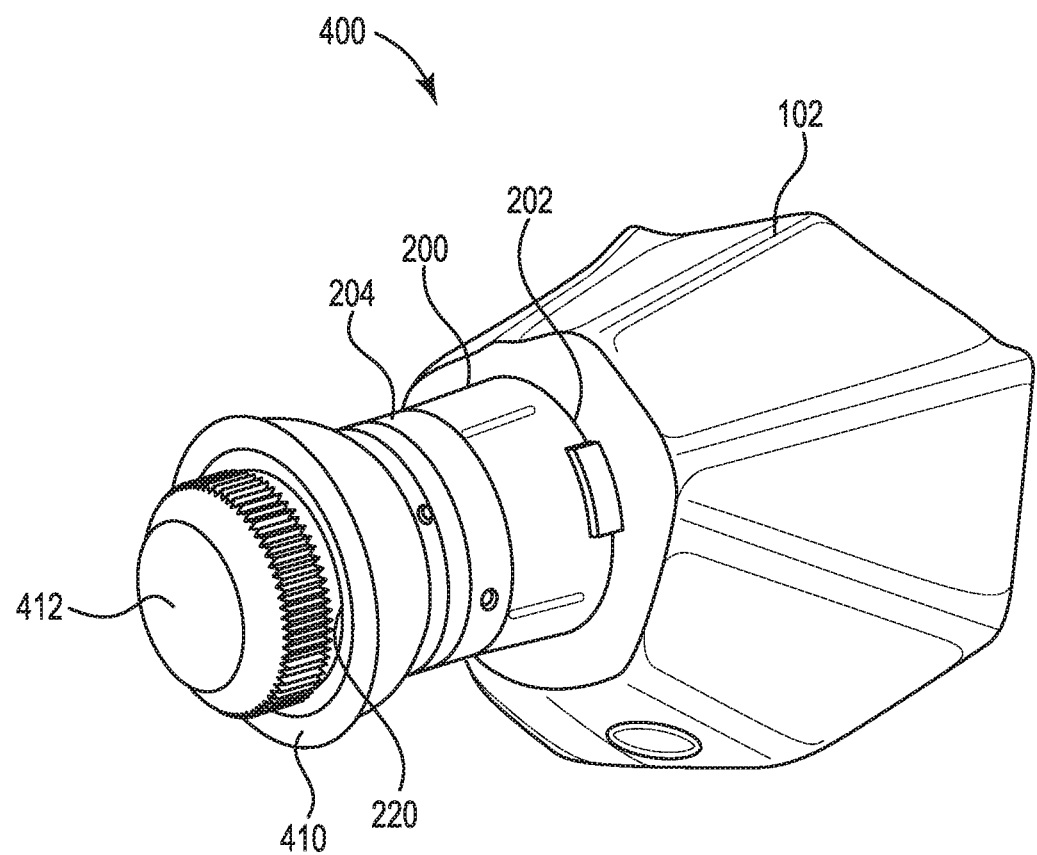
FIGS. 3A-3B illustrate perspective views of a second sampling interface member on a handheld device housing and a view of a portion of the second sampling member without the mounting sleeve, respectively, according to an example embodiment of the invention.
Figure 3B:
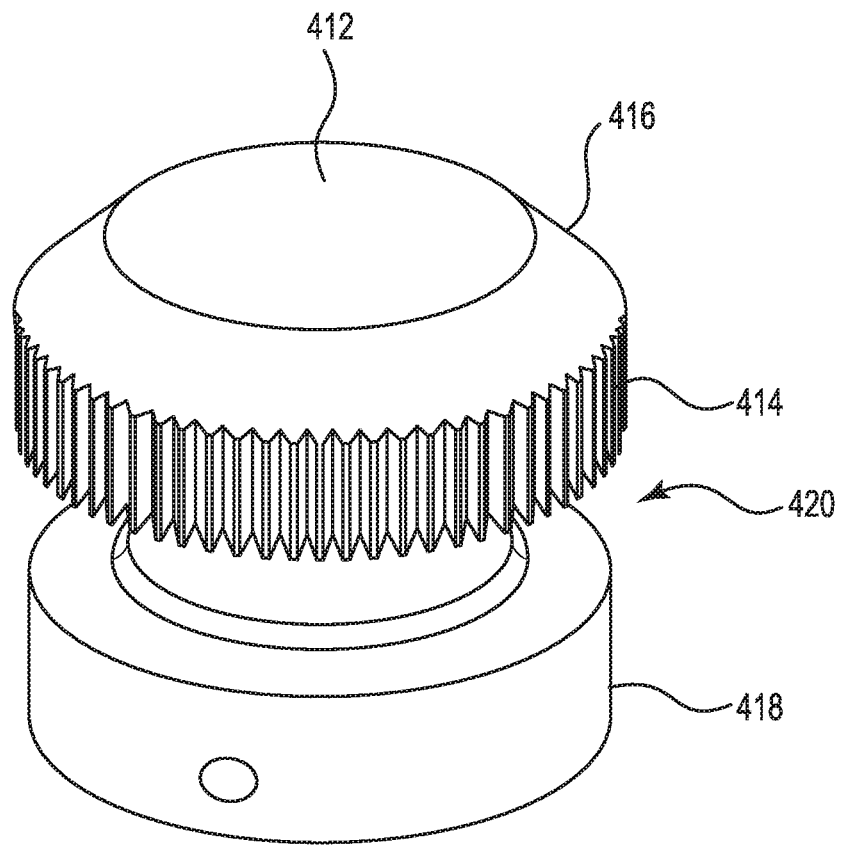

Referring now to FIGS. 3A-3B, there are illustrated perspective views of a second sampling interface member 400 on handheld RAMAN device 102 which includes a concave portion or plunger member 410 and a pellet holder or plug interface 412, respectively, without the mounting sleeve, according to an example embodiment of the invention. In this example embodiment, pellet holder or interface 412 (with corrugated side surface 414) helps to secure sample spectrographic measurements or readings from pellet-sized samples. In this example, pellet holder 412 structurally comprises an upper disc member 416 and a lower disc member 418 with an interposing cylinder 420.

Figure 3C:
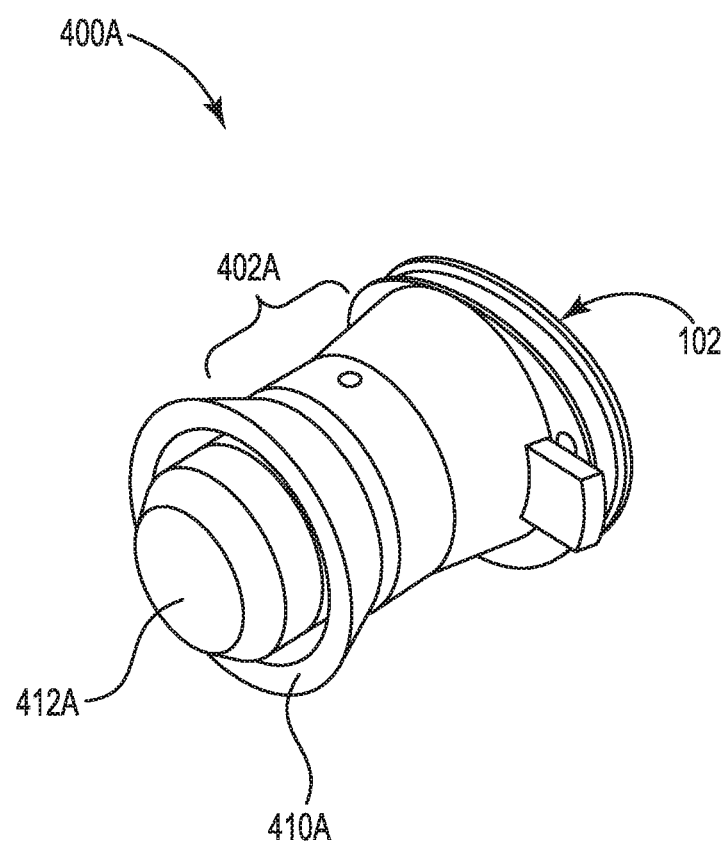
FIGS. 3C-3D illustrate a perspective view of a modified second sampling interface member on a handheld device housing and an exploded view of the modified second sampling member, respectively, according to an example embodiment of the invention.
Figure 3D:
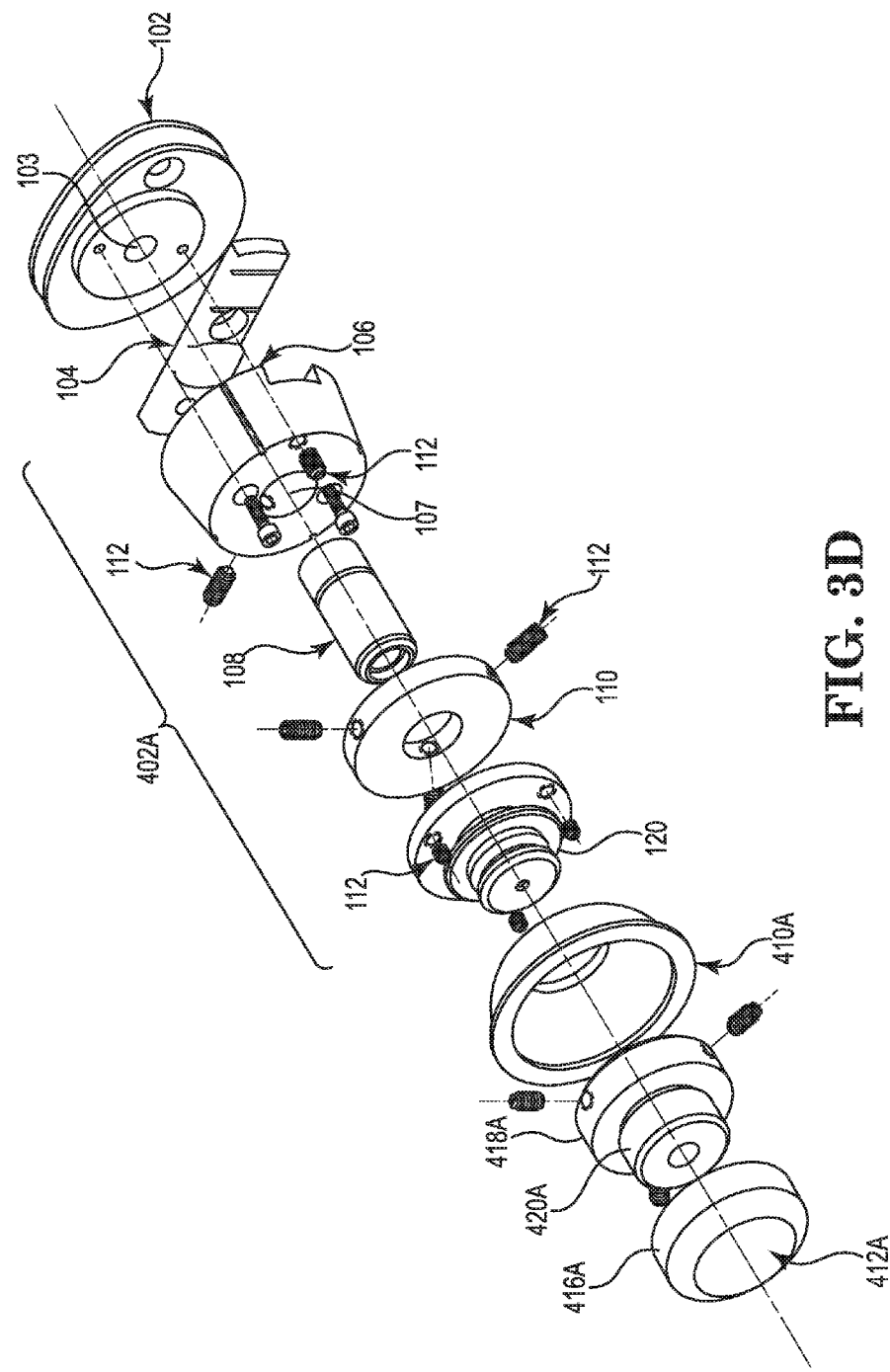

FIGS. 3C-3D illustrate a perspective view of a modified second sampling interface member (or sampling head assembly) 400A for placement on a handheld spectrographic measurement device housing and an exploded view of the modified second sampling member, respectively. In particular, interface member 400A includes a concave portion or plunger member 410A and a pellet holder or interface 412A, respectively, according to an example embodiment of the invention. In this example embodiment, pellet holder or interface 412A helps to acquire sample spectrographic measurements or readings from secured pellet-sized samples. In this example, pellet holder 412A structurally comprises an upper disc member 416A and a lower disc member 418A with an interposing cylinder 420A. In this example embodiment, sampling head assembly 400A includes a subassembly 402A comprising a collection interface member 102 having a central aperture 103 for placement over the handheld device housing exit. Next, a calibration holder or tab 104 is located adjacent interface member 102 and then a calibration clamp member 106 is disposed adjacent to holder 104 and collection interface member 102. Clamp member 106 includes an aperture 107 that is disposed collinear with central aperture 103 of the collection interface member. A sampling tube member 108 is disposed through and collinear with calibration clamp member 106 with a proximal end of tube member 108 disposed over central aperture 103 of collection interface member 102. A cover stopper member 110 is then located at one end of sampling tube 108 and is held in place by a series of set screws 112. A sampling tube cover member 120 is then disposed over a distal end of sampling tube member 108 and adjacent cover stopper 110, thereby forming subassembly 402A of sampling head assembly 400A.

Figure 4A:
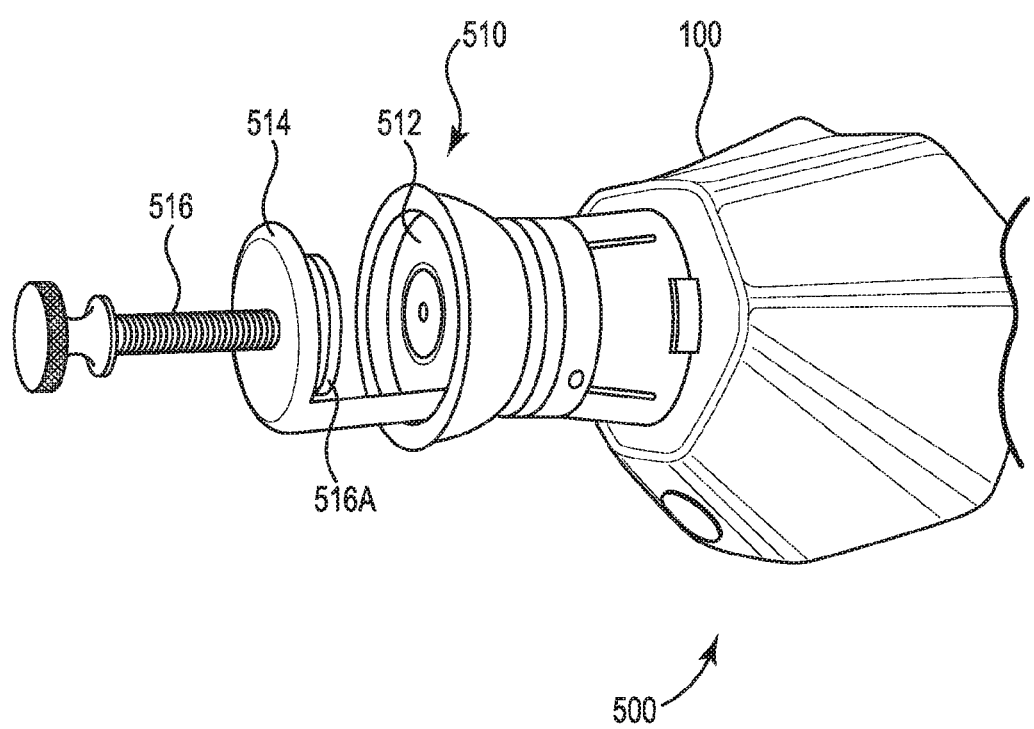
FIGS. 4A-4B illustrate perspective views of a third sampling interface member on a handheld device and a view of a portion of the third sampling member without the mounting sleeve, respectively, according to an example embodiment of the invention.
Figure 4B:
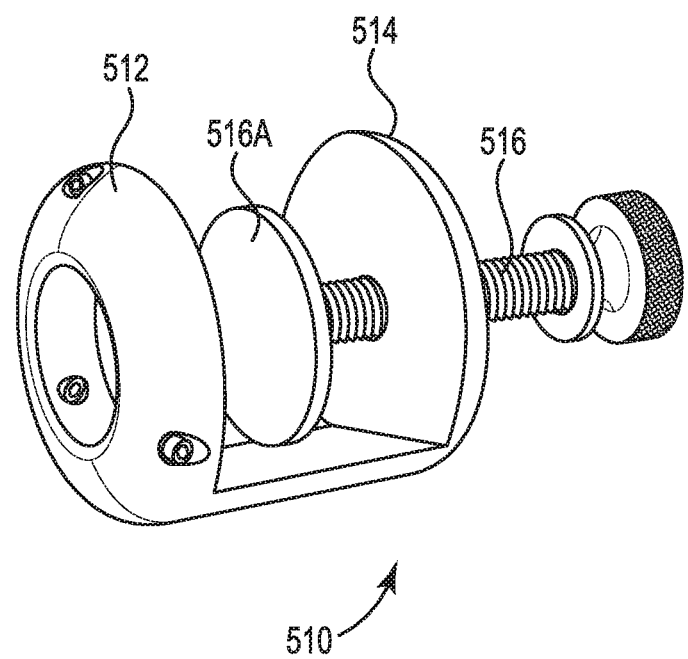

Referring now to FIGS. 4A-4B, there are illustrated perspective views of a third sampling interface member 500 on a handheld RAMAN device 100 and a portion or assembly 510 of the third sampling member, without the mounting sleeve, according to an example embodiment of the invention. In this example embodiment, sampling head assembly 510 includes an interface plug 512, which is in contact with the distal end of the mounting sleeve 200, a plastic sheet interface 514, which is attached to plug 512, and a thumbscrew 516 and pad 516A, all of which help secure the irregularly shaped or odd shaped sample piece or sample particle between thumbscrew pad 516A and interface plug 512 to improve measurement accuracy.

Figure 4C:
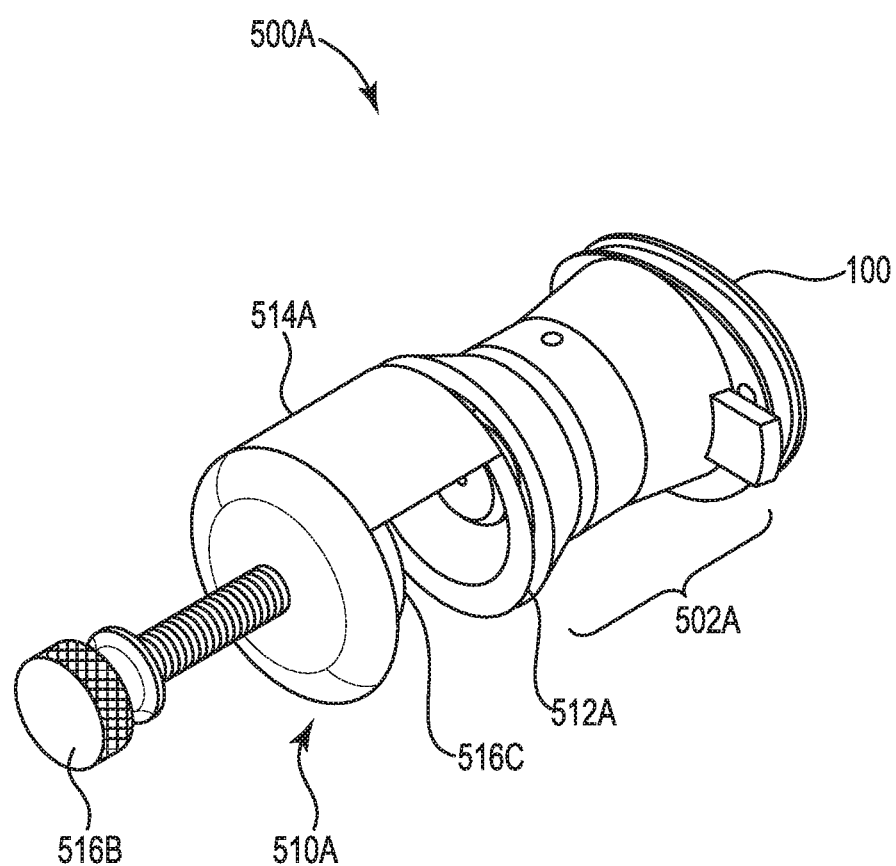
FIGS. 4C-4D illustrate perspective views of a modified third sampling interface member on a handheld device and an exploded view of a portion of the modified third sampling member, respectively, according to an example embodiment of the invention.
Figure 4D:
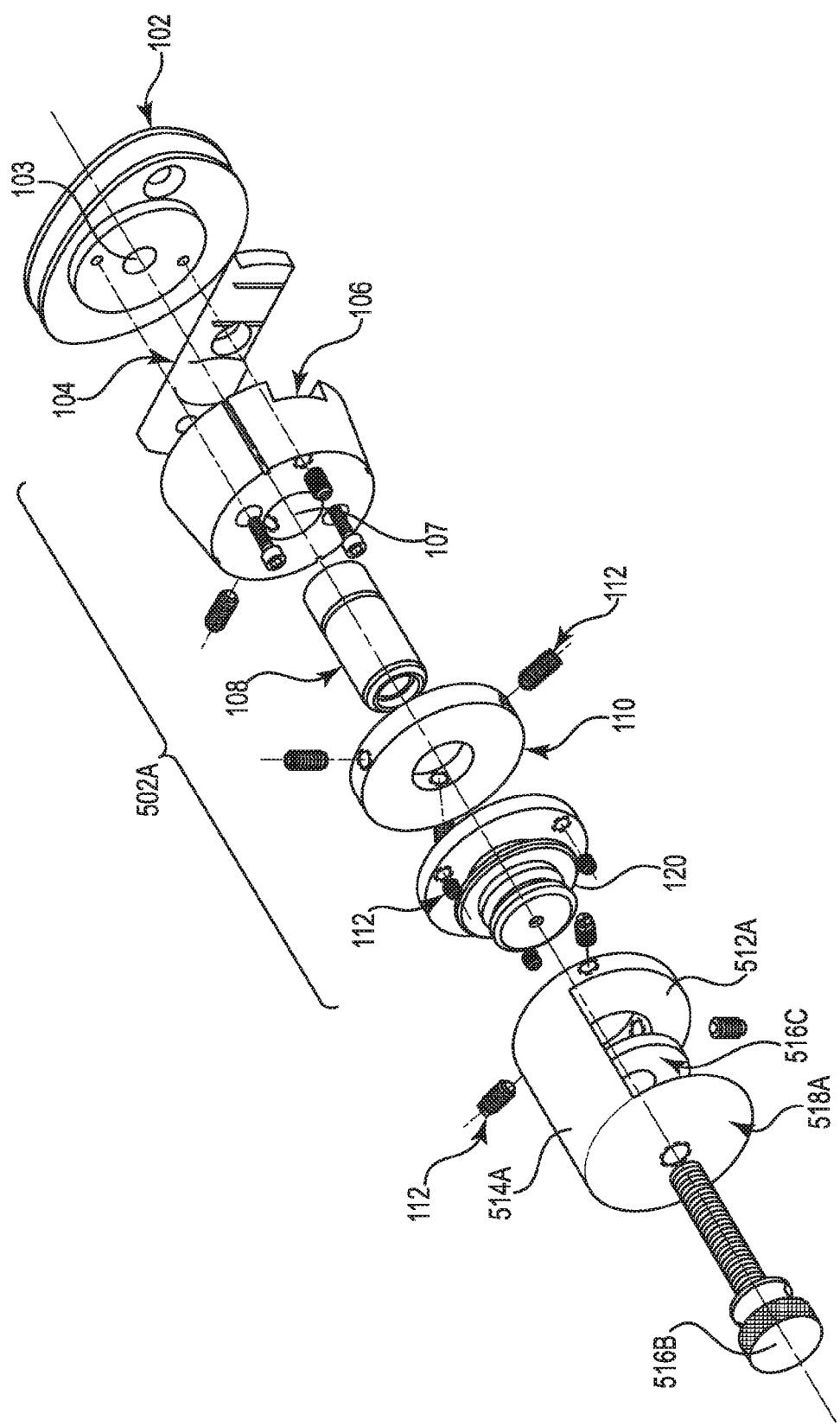

FIGS. 4C-4D illustrate perspective views of a modified third sampling interface member 500A (with subassembly 502A) on a handheld device 100 and an exploded view of a portion of the third sampling member, respectively, according to an example embodiment of the invention. In this example embodiment, sampling head assembly 510A includes an interface plug 512A, a plastic (or other sturdy materials) sheet interface 514A, and a thumbscrew 516B and pad 516C, all of which help secure the irregularly shaped or odd shaped sample piece or sample particle between thumbscrew pad 516B and interface plug 512A to improve measurement accuracy. In this example embodiment, sampling head assembly 500A includes a subassembly 502A comprising a collection interface member 102 having a central aperture 103 for placement over a handheld spectrographic measurement device housing exit. Next, a calibration holder or tab 104 is located adjacent interface member 102 and then a calibration clamp member 106 is disposed adjacent to holder 104 and collection interface member 102. Clamp member 106 includes an aperture 107 that is disposed collinear with central aperture 103 of collection interface member 102. A sampling tube member 108 is disposed through and collinear with calibration clamp member 106 with a proximal end of sampling tube member 108 disposed over central aperture 103 of collection interface member 102. A cover stopper member 110 is then located at one or distal end of sampling tube 108 and is held in place by a series of set screws 112. A sampling tube cover member 120 is then disposed over a distal end of sampling tube member 108 and adjacent cover stopper 110, thereby forming subassembly 502A of sampling head assembly 500A.

Figure 5:
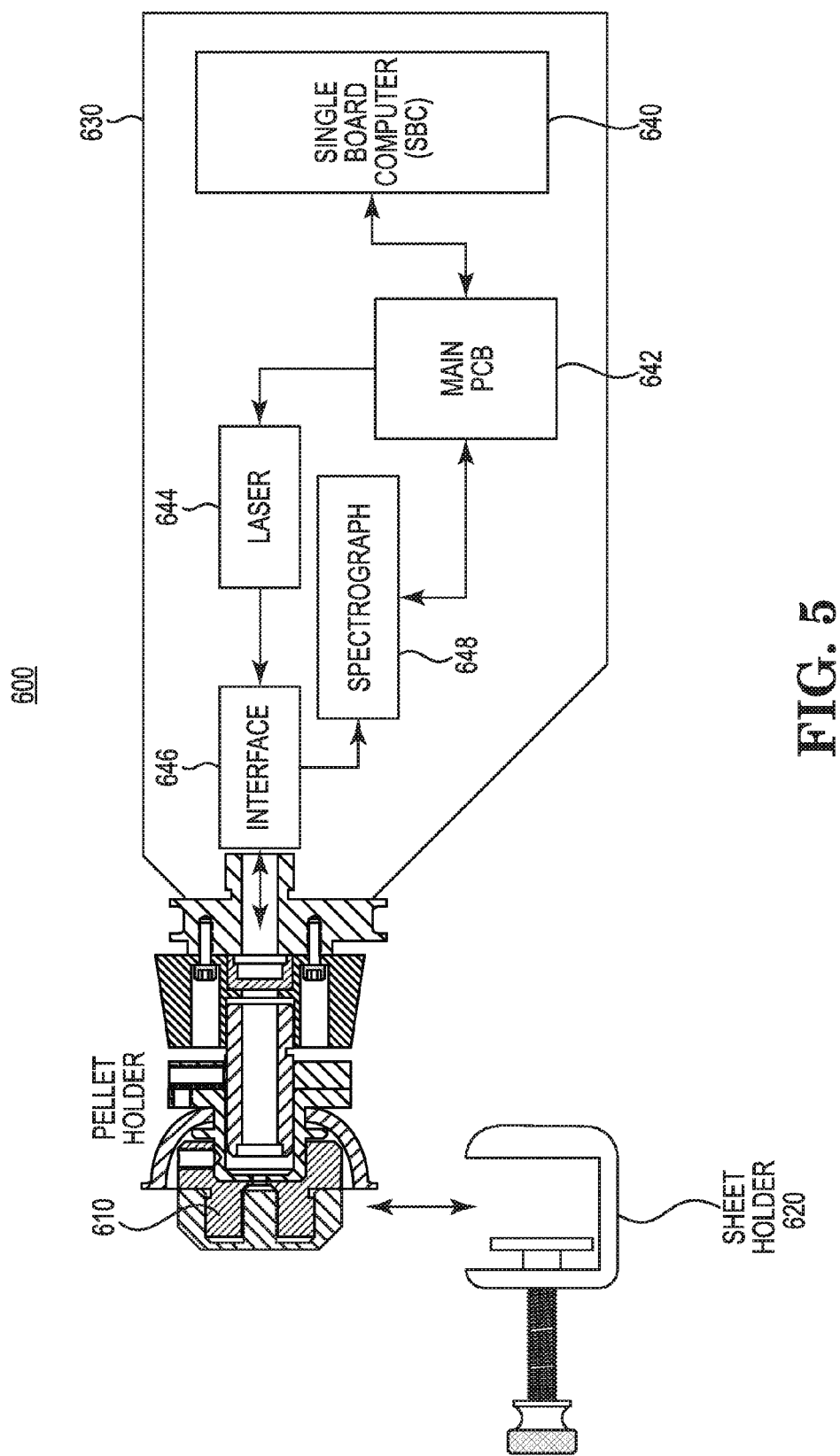
FIG. 5 illustrates a schematic view of a handheld spectroscopy measurement system with an interchangeable sampling head and a side view of a clamping-type sampling head, respectively, according to an example embodiment of the invention.

FIG. 5 illustrates a schematic view of a handheld spectroscopy measurement system 600 with an interchangeable sampling head 610 and a side view of a clamping-type sampling head 620, respectively, according to an example embodiment of the invention. In particular, system 600 includes a housing 630 that houses a single board computer or microprocessor 640 that is communicatively coupled to a main printed circuit board (PCB) 642. PCB 642 is communicatively coupled to a laser module 644 which is an electromagnetic radiation source that emits energy through interface module 646 and through a housing exit (not shown) through either sampling heads 610 or 620. Radiation received from the sample material and through interface 646 is directed to spectrometer module 648, the data of which is routed back to PCB 642 and to controller 640 for processing. Controller 640 also controls the triggering of laser module 644 and the capture of the radiation by spectrograph 648. In this example embodiment, laser module 644 is a wavelength stable laser source, such as but not limited to Nd:YAG, which projects a laser beam through the housing exit and the interaction assembly and onto the sample material.

In one example embodiment, an apparatus is provided for interfacing a handheld Raman spectroscopy apparatus with a sample material, the apparatus including an electromagnetic radiation source and an electromagnetic radiation detection and processing module. The apparatus also includes a housing configured to have an exit for the electromagnetic radiation and for capture of an emitted electromagnetic radiation from the sample material and includes a housing-to-sample material interaction assembly or section disposed about the housing exit. In one example embodiment, the housing-to-sample interaction section is disposed at a distal end of a mounting sleeve having a tube cover assembly thereon adapted to reduce light interference during measurement. In a related example embodiment, the interaction assembly includes a mounting sleeve having a calibration tab formed at a proximal end and a sampling interface assembly located at a proximal end of the mounting sleeve, the sampling interface assembly including a cover assembly and a radiation probe member disposed at least partially therein. In this example embodiment, the cover assembly includes a concave portion at a proximal end and an open distal end, the cover assembly further having a substantially flat surface at the proximal end and sidewalls protruding up therefrom toward the open distal end. In a related example embodiment, the cover assembly includes a tube cover assembly and the radiation probe member includes a tube cover stopper disposed in the concave portion of the tube cover assembly, the tube cover stopper including an elongate aperture therethrough for exposing the electromagnetic radiation from the electromagnetic radiation source and wherein the tube cover stopper is concentrically disposed within the concave portion of the tube cover assembly and protrudes up therefrom. In various example embodiments, the cover assembly has a concave structure with a shape selected from the group consisting of a cylinder, bowl, a square box, a rectangular box and an elliptical bowl.

In a related embodiment, the housing-to-sample interaction assembly or section is disposed at a distal end of a mounting sleeve having a pellet interface member thereon adapted to sharpen the focus of the measurement cylinder member. In this example embodiment, the radiation probe member includes a substantially cylindrical pellet member located within a concave portion of the cover assembly adapted to sharpen the focus of the measurement cylinder member, the cylindrical pellet member partially protruding up beyond the open distal end of the cover assembly and including a substantially flat upper sampling surface, wherein the cylindrical pellet member is comprised of an upper sampling disc and a lower engaging disc which engages the concave portion of the cover assembly and an elongate portion interposed between the upper and lower discs.

In another related embodiment, the housing-to-sample interaction section is disposed at a distal end of a mounting sleeve having a clamping style interface assembly, the clamping style interface assembly including an interface plug, a plastic sheet interface member and a thumbscrew and a thumbscrew interface pad member thereon adapted to grasp or clamp irregularly shaped sampled material.

The various embodiments described herein are not necessarily limited to RAMAN devices as they are applicable to LIBS and XRF devices as well.

The following patents that relate to such RAMAN devices are herein incorporated by reference in their entirety and constitute part of the disclosure herein: U.S. Pat. Nos. 7,548,310; 7,505,128; and 8,699,020.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

What is claimed is:

1. An apparatus for interfacing a handheld Raman spectroscopy apparatus with a sample material, the handheld spectroscopy apparatus including an electromagnetic radiation source and an electromagnetic radiation detection and processing module, the interfacing apparatus comprising:
   a housing for the handheld apparatus configured to have an exit for the electromagnetic radiation and for capture of an emitted electromagnetic radiation from the sample material; and
   a housing-to-sample material interaction assembly disposed about the housing exit, the interaction assembly including a mounting sleeve having a calibration tab formed at a proximal end and an sampling interface assembly located at a proximal end of the mounting sleeve, the sampling interface assembly including a cover assembly and a radiation probe member disposed at least partially therein, wherein the sampling interface assembly is adapted to reduce light interference during a Raman measurement.

2. The interfacing apparatus according to claim 1, wherein the cover assembly includes a concave portion at a proximal end and an open distal end, the cover assembly further having a substantially flat surface at the proximal end and sidewalls protruding up therefrom toward the open distal end.

3. The interfacing apparatus according to claim 2, wherein the cover assembly includes a tube cover assembly and the radiation probe member includes a tube cover stopper disposed in the concave portion of the tube cover assembly, the tube cover stopper including an elongate aperture therethrough for exposing the electromagnetic radiation from the electromagnetic radiation source.

4. The interfacing apparatus according to claim 2, wherein the tube cover stopper is concentrically disposed within the concave portion of the tube cover assembly and protrudes up therefrom.

5. The interfacing apparatus according to claim 2 wherein the cover assembly has a concave structure with a shape selected from the group consisting of a cylinder, bowl, a square box, a rectangular box and an elliptical bowl.

6. The interfacing apparatus according to claim 2, wherein the radiation probe member includes a substantially cylindrical pellet member located within a concave portion of the cover assembly adapted to sharpen the focus of the measurement cylinder member, the cylindrical pellet member partially protruding up beyond the open distal end of the cover assembly and including a substantially flat upper sampling surface.

7. The interfacing apparatus according to claim 6, wherein the cylindrical pellet member is comprised of an upper sampling disc and a lower engaging disc which engages the concave portion of the cover assembly and an elongate portion interposed between the upper and lower discs.

8. The interfacing apparatus according to claim 1, wherein the sample interaction assembly further includes a clamping-type interface assembly disposed at the distal end of the mounting sleeve and partially within the cover assembly, the clamping-type interface assembly including an interface plug portion coupled to a first end of an elongate interposing member, the elongate interposing member coupled at a second end to a thumbscrew pad assembly, wherein the clamping-type interface assembly is adapted to clamp or grasp an irregularly shaped sampled material against the housing exit.

9. The interfacing apparatus according to claim 8, wherein the interface plug portion includes an aperture and wherein the plug portion is configured to fit within the cover assembly with the aperture fitting around the radiation probe member.

10. The interfacing apparatus according to claim 1, wherein the electromagnetic radiation source is a wavelength stable laser configured to project a laser beam through the housing exit and the interaction assembly and onto the sample material.

11. A sampling head assembly for use on a handheld spectroscopy device, the handheld spectroscopy device including an electromagnetic radiation source, an electromagnetic radiation detection and a processing module located within a housing having a housing exit for electromagnetic radiation and for capture of an emitted electromagnetic radiation from a sample material, the sampling head assembly comprising:
   a collection interface member having a central aperture for placement over the housing exit;
   a calibration clamp member disposed adjacent to the collection interface member, the clamp member with an aperture disposed collinear with the central aperture of the collection interface member;

a sampling tube member disposed through and collinear with the calibration clamp member with a proximal end of the tube member disposed over the central aperture of the collection interface member; and a sampling tube cover member disposed over a distal end of a sampling tube member, thereby forming the sampling head assembly.

12. The sampling head assembly according to claim 11 further comprising a calibration clamp holder for holding and axially moving the calibration clamp member and a cover stopper member interposed between the sampling tube and the sampling tube cover member.

13. The sampling head assembly according to claim 11 further comprising a concave member having an open end and an aperture opposite the open end, the concave member disposed adjacent to the sampling tube cover member with a portion of the sampling tube cover member protruding through the concave member aperture, wherein the concave member is adapted to reduce light interference during a spectrographic measurement.

14. The sampling head assembly according to claim 13 further comprising a pellet holder assembly disposed over the sampling tube cover member, the pellet holder assembly including a pellet holder with a proximal end disposed on the tube cover member and a pellet holder cover disposed on a distal end of the pellet holder, wherein the pellet holder assembly is adapted to reduce light interference during a spectrographic measurement.

15. The sampling head assembly according to claim 13 further comprising a clamping-type interface assembly disposed in contact with a distal end of the sampling tube cover member, the clamping-type interface assembly including an interface plug portion coupled to a first end of an elongate interposing member, the elongate interposing member coupled at a second end to a thumbscrew pad assembly, wherein the clamping-type interface assembly is adapted to clamp or grasp an irregularly shaped sampled material against the housing exit, thereby reducing light interference during a spectrographic measurement.

16. The sampling head assembly according to claim 13 wherein the concave member has a concave structure with a shape selected from the group consisting of a concave plunger or bowl, a square box, a rectangular box and an elliptical bowl.

17. The sampling head assembly according to claim 11 configured to operate with a spectrographic measurement device selected from the group consisting of Raman, LIBS, fluorescence and x-ray radiation.

18. A handheld Raman spectroscopy apparatus for performing spectrographic measurements on a sample material, the Raman handheld spectroscopy apparatus having a housing configured to have an exit for electromagnetic radiation and for capture of an emitted electromagnetic radiation from the sample material, the Raman handheld apparatus comprising:

a laser module for emitting electromagnetic radiation on the sample material;

a spectrometer module for receiving and detecting electromagnetic radiation received from the sample material;

a processing module communicatively coupled to the laser module and the spectrometer module disposed within the housing, the processing module configured to control energization of the laser module and processing of spectrographic measurements received from the spectrometer module; and a housing-to-sample material interaction assembly disposed about the housing exit wherein a distal end of the interaction assembly is configured to receive interchangeable sampling heads that reduce light interference during a Raman measurement of sampled materials having different shapes and sizes, the interaction assembly including:

a collection interface member having a central aperture for placement over the housing exit;

a calibration clamp member disposed adjacent to the collection interface member, the clamp member with an aperture disposed collinear with the central aperture of the collection interface member;

a sampling tube member disposed through and collinear with the calibration clamp member with a proximal end of the tube member disposed over the central aperture of the collection interface member; and a sampling tube cover member disposed over a distal end of a sampling tube member, a distal end of the tube cover member configured to receive the interchangeable sampling heads.

19. The handheld apparatus according to claim 18, further comprising a concave plunger member and a pellet holder assembly disposed over the sampling tube cover member, the pellet holder assembly including a pellet holder with a proximal end disposed on the tube cover member and a pellet holder cover disposed on a distal end of the pellet holder, wherein the pellet holder assembly is adapted to hold the sample material so as to reduce light interference during a spectrographic measurement.

20. The handheld apparatus according to claim 19, further comprising a clamping-type interface assembly disposed in contact with a distal end of the sampling tube cover member, the clamping-type interface assembly including an interface plug portion coupled to a first end of an elongate interposing member, the elongate interposing member coupled at a second end to a thumbscrew pad assembly, wherein the clamping-type interface assembly is adapted to clamp or grasp an irregularly shaped sample material against the housing exit, thereby reducing light interference during a spectrographic measurement.

* * * * *